United States Patent [19]

Child et al.

[11] Patent Number: 5,258,568
[45] Date of Patent: Nov. 2, 1993

[54] SINGLE PATH ALKYLATION METHOD EMPLOYING REDUCED ACID INVENTORY

[75] Inventors: Jonathan E. Child; Tomas R. Melli, both of Sewell, N.J.; Sergei Yurchak, Media, Pa.

[73] Assignee: Mobil Oil Corp., Fairfax, Va.

[21] Appl. No.: 965,306

[22] Filed: Oct. 23, 1992

[51] Int. Cl.$^5$ .............................. C07C 2/56; C07C 2/58
[52] U.S. Cl. ................................ 585/710; 585/709; 585/721; 585/723; 585/731; 502/34; 502/38
[58] Field of Search ............... 585/723, 731, 709, 710, 585/721; 502/34, 38

[56] References Cited

U.S. PATENT DOCUMENTS

| | | |
|---|---|---|
| 2,353,119 | 7/1944 | Workman . |
| 2,937,079 | 5/1960 | Van Pool . |
| 4,090,943 | 5/1978 | Moll et al. . |
| 4,148,836 | 4/1979 | Sturtevant et al. . |
| 5,008,001 | 4/1991 | Kitamura et al. . |
| 5,095,167 | 3/1992 | Christensen . |
| 5,607,970 | 9/1971 | Borst, Jr. ........................ 585/710 |

FOREIGN PATENT DOCUMENTS 9203395  3/1992  PCT Int'l Appl. .

*Primary Examiner*—Patrick P. Garvin
*Assistant Examiner*—E. D. Irzinski
*Attorney, Agent, or Firm*—Alexander J. McKillop; Dennis P. Santini

[57] ABSTRACT

A single path process for alkylating a hydrocarbon feedstock containing an olefin and an isoparaffin is disclosed. The process includes dispersing an acid-based liquid alkylation catalyst into a reaction zone for contact with a continuous hydrocarbon phase. The process further includes separating the hydrocarbon phase from the acid catalyst upon completion of the alkylation reaction and providing a continuous on-line regeneration of the entire volume of catalyst once it has been separated from the hydrocarbon phase.

18 Claims, No Drawings

SINGLE PATH ALKYLATION METHOD EMPLOYING REDUCED ACID INVENTORY

BACKGROUND OF THE INVENTION

The present invention relates to the petroleum refining industry and, more particularly to an alternative approach for alkylating a hydrocarbon feedstock. Specifically, the present invention is an alternative alkylation process involving an acid-dispersion-based alkylation reaction followed by a hydrocarbon/acid-catalyst separation and a continuous on-line regeneration of the total volume of acid catalyst employed in the operation.

Alkylation is a reaction in which an alkyl group is added to an organic molecule. In petroleum chemistry, alkylation involves reacting isobutane or other isoparaffins with olefins in the presence of a strong H. donor, such as a strong acid, in order to produce high octane paraffins which boil in the range of gasoline. In short, an isoparaffin starting material can be reacted with an olefin to produce an isoparaffin product having a higher molecular weight. Industrial alkylation processes generally depend upon the reaction of a $C_2$ to $C_5$ olefin with isobutane in the presence of an acid-based catalyst in order to produce an alkylate product. These alkylate products are valuable blending components in the manufacture of gasoline due to their high octane rating and their sensitivity to octane-enhancing additives.

Industrial alkylation processes have historically used hydrofluoric or sulfuric acid catalysts under relatively low temperature conditions. For example, sulfuric acid alkylation reaction is particularly sensitive to temperature, with low temperatures being favored in order to minimize the side reaction of olefin polymerization. Petroleum refinery technology favors alkylation over polymerization because larger quantities of higher octane products can be produced per available light chain olefins. Acid strength in these liquid acid catalyzed alkylation processes is preferably maintained at 88 to 94% by weight using the continuous addition of fresh acid and the continuous withdrawal of spent acid.

Conventional alkylation processes generally take place in three stages. The first stage, known as the reaction stage, takes place in a reactor where hydrocarbon reactants, such as isobutane and olefins, are dispersed into a continuous acid phase. The second stage, known as the separation stage, typically takes place in a settling vessel where the hydrocarbon phase and the acid phase are separated using conventional gravity separation techniques. The third stage involves a heat-exchanging procedure as well as a continuous regeneration of a small portion of the acid-based catalyst using what is known as a "slip stream".

As previously mentioned, conventional alkylation units employed in the oil refining industry typically utilize strong acids, such as HF or $H_2SO_4$, as a reaction catalyst. Each of the three stages previously mentioned take place in a separate area or vessel and involve large volumes of acid. For example, in the reactor vessel, hydrocarbon reactants (olefins and isobutane) are dispersed into a continuous acid phase, typically HF, where they react in the presence of the acid catalyst to produce an alkylate product. During the alkylation reaction, a portion of the acid catalyst becomes "spent" or unsuitable for further catalysis of the alkylation reaction. As a result, this spent catalyst must either be regenerated or replaced. In order to minimize costs and maximize efficiency, conventional alkylation techniques utilize large volumes of acid in order to reduce the frequency of acid regeneration and/or acid replacement operations as well as avoiding sudden decreases in acid strength.

Once the alkylation reaction has gone to completion, the reaction mixture is subsequently transferred to a separation vessel where the alkylate product and any unreacted hydrocarbons are separated from the acid phase using conventional gravity separation techniques. Once the separation is completed, the acid phase is removed and transferred to a heat-exchanger where the heat accruing from the exothermic alkylation reaction is dissipated. The acid phase is subsequently returned to the reactor vessel to perform additional catalysis.

Conventional alkylation technology does not utilize the acid only as a proton-donating catalyst for the reaction, but also incorporates the acid to provide a medium for dissipating heat given off by the exothermic alkylation reaction. Larger volumes of the acid catalyst provide more heat-dissipation capability, thereby reducing the necessity for frequent heat-exchanging operations. Consequently, conventional alkylation units also utilize large acid inventories for more efficient heat dissipation.

In addition to its catalytic and heat dissipation roles, the acid catalyst also provides a medium in which undesirable by-products form. The multi-functional role of the acid has further led refinery operators to incorporate large volumes of acid throughout the three stage alkylation process. For example, it is well known that the volume of available functional catalyst decreases as the alkylation reaction proceeds because the acid phase becomes contaminated with undesirable by-products, such as acid soluble oil; i.e. "ASO". Consequently, the acid must be periodically regenerated or replaced otherwise the reaction performance will drop to unacceptable levels.

In a typical regeneration process for HF acid, the acid catalyst is stripped away from the undesirable by-products or contaminants using isobutane and the recovered acid is eventually shunted back to the reaction vessel after undergoing heat-exchange. Generally, the volume of acid catalyst is large enough so that complete regeneration of the catalyst only occurs about twice a day. As previously mentioned, once the hydrocarbon phase, which includes the olefinic and isoparaffinic reactants, has been dispersed into the continuous acid phase and given time to react, the reaction mixture is shunted to a separation or settling vessel where the mixture of acid and hydrocarbons undergoes a gravity induced separation. The acid migrates to the bottom of the vessel and is transferred to a heat-exchanging unit. After adequate heat dissipation has occurred, the acid is subsequently shunted back to the reactor vessel to further catalyze reactions. A small portion of the returning acid catalyst (about 0.01 percent of the total volume) is continuously shunted away to a regeneration zone in what is commonly referred to as a "slip-stream". Once the acid catalyst present in the slip-stream has undergone regeneration, it is returned to the reaction vessel to perform further catalysis.

Sulfuric acid catalysts can not be regenerated by stripping with isobutane. Sulfuric acid catalysts are regenerated by reacting the spent catalyst with oxygen at high temperature to form $SO_2$ which is then exposed to additional oxygen and converted to $SO_3$. Fresh sulfuric acid is then made by contacting $SO_3$ with water.

Conventional alkylation techniques incorporate the methods mentioned above in order to provide the reaction vessel with a constant influx of fresh acid catalyst. In addition to performing a heat dissipation and a catalysis function, this influx of fresh catalyst ensures that the concentration of undesirable by-products does not accumulate to the point that the overall yield of alkylate product is reduced. If the by-product concentration becomes too high, there is a rapid downturn in the yield of alkylate product, because the catalyst will tend to catalyze undesirable reactions between by-products at high concentrations of these contaminants.

As previously mentioned, conventional alkylation technology incorporates large volumes of acid-based catalysts in all three stages of the alkylation operation. This situation is especially problematic when the alkylation procedure incorporates large volumes of noxious liquid acid catalysts, such as HF or $H_2SO_4$. An accidental release of an appreciable volume of these acids can have an extremely deleterious effect on the environment.

In particular, large volumes of these acids are employed in the reaction zone in order to dissipate the heat of reaction, to reduce a rapid increase in the concentration of undesirable by-products and to reduce the frequency of acid regeneration and/or acid replacement operations. Additionally, many conventional alkylation processes employ gravity separation vessels which retain large volumes of the hydrocarbon/acid reaction mixture. Anytime a large volume of strong acid is contained at a refinery site for an extended period of time, there is an increased probability for an accidental release of the acid into the environment. Consequently, there is a need for alternative alkylation processes which avoid the environmental and safety concerns associated with conventional alkylation techniques employing large quantities of acid.

While there have been attempts to develop alkylation methods which employ a reduced volume of acid catalysts, these approaches often lack the efficiency necessary for practical implementation into an industrial refinery setting. Typical problems encountered in using a reduced acid inventory include rapid decreases in acid strength, rapid increases in the concentration of undesirable by-products, rapid temperature increases due to the exothermic heat of reaction and rapid increases in the concentration of spent catalyst. Consequently, there is a need for alternative alkylation processes which address the typical problems associated with alkylation techniques employing reduced acid inventories.

It is therefore an object of the present invention to provide an alternative alkylation process utilizing a reduced acid inventory in order to promote safety and minimize the impact of an accidental release of the acid catalyst into the environment.

It is further an object of the present invention to provide an alternative alkylation process which is a viable candidate for implementation into an industrial refinery setting.

SUMMARY OF THE INVENTION

The present invention is a single path process for alkylating a hydrocarbon feedstock containing an olefin and an isoparaffin. The process includes dispersing an acid-based liquid alkylation catalyst into a reaction zone for contact with a continuous hydrocarbon phase containing effective amounts of olefinic and isoparaffinic starting materials sufficient for the formation of an alkylate product. The method further includes separating the continuous hydrocarbon phase from the acid-based liquid catalyst upon completion of the alkylation reaction and providing a continuous on-line regeneration of the entire volume of the catalyst once it has been separated from the hydrocarbon phase. The process further involves returning the regenerated catalyst to the reaction zone where it is redispersed for subsequent contact with the continuous hydrocarbon phase.

In a conventional alkylation process, the hydrocarbon reactants are dispersed in a continuous acid phase (a liquid-liquid dispersion). Typically, the acid inventory is of a high volume for the reasons previously mentioned. Quite differently, the present invention involves dispersing a liquid acid-based catalyst into a continuous hydrocarbon phase. The process utilizes an extremely low acid inventory relative to conventional alkylation methods. In particular, the total acid inventory in the reactor area is 40 to 100 times less than in any of the existing alkylation technologies.

Since the method of the present invention drastically reduces the volume of acid present during alkylation, there is a rapid increase in the concentration of undesirable by-products. Additionally, the volume of functional catalyst available to catalyze the alkylation reaction is depleted more rapidly. The method of the present invention addresses this problem by utilizing a continuous, on-line regeneration approach wherein all of the catalyst is continually shunted to the regeneration zone after each reaction run rather than employing a conventional "slip-stream" regeneration approach.

Furthermore, conventional alkylation processes generally employ gravity separation, as previously mentioned. During the separation process, the hydrocarbon/acid mixture from the reaction vessel is incubated in a separation vessel until adequate separation has been achieved. Consequently, separation vessels will typically contain large volumes of acid during the settling period.

In a preferred embodiment of the method of the present invention, a hydrocyclonic separation technique is employed in order to promote the separation of the hydrocarbon and acid components, thereby decreasing separation times. In particular, hydrocyclones are induced by passing the reaction mixture through conical vessels located in the separation zone. Due to the configuration of the vessels, the flow velocity of the entering mixture increases as the mixture progresses further into the vessels. The heavier substances, i.e. the acid phase, moves more rapidly to the outside of the vessel, thereby facilitating a decreased separation time. Accordingly, it is preferred to incorporate hydrocyclonic separation in the method of the present invention in order to optimize the efficiency of the process, since conventional separation techniques may not be rapid enough to promote efficient separation at such low volumes of the acid catalyst.

The incorporation of hydrocyclonic separation techniques into the method of the present invention affords further advantages in limiting the volume of acid catalyst utilized for the alkylation process. For example the use of hydrocyclonic separation affords refinery operators with the option to reduce the acid inventory in the separation zone to a volume as low as 50 gallons in contrast to conventional alkylation techniques where as much as 2000–5000 gallons of acid are present during the separation operation.

Additionally, the reduced volume of acid catalyst incorporated in the method of the present invention affords certain advantages over prior art alkylation techniques with respect to additive concentrations. For example, certain additives are added to the reaction mixture. These additives are typically provided in order to reduce the vapor forming tendency of strong acid catalysts, such as HF, and consequently reduce the risk of accidental vapor cloud formation when the acid is present in the separation and regeneration zones. Due to the presence of a reduced acid inventory afforded by the method of the present invention, an appreciably smaller volume of these additives is required in order to achieve the same net concentration, since there is a smaller overall volume of acid present throughout the separation and regeneration steps. Consequently, the method of the present invention affords an added advantage in reducing the overall costs associated with the alkylation operation.

Additionally, the method of the present invention affords the use of short lived, high activity alkylation catalysts since the entire volume of catalyst is continuously shunted to the regeneration zone after each reaction run.

For a better understanding of the present invention, together with other and further objects, reference is made to the following description, the scope of which will be pointed out in the appended claims.

DETAILED DESCRIPTION OF THE INVENTION

The present invention is an alternative process for alkylating a hydrocarbon feedstock containing olefins and isoparaffins. The process involves dispersing an acid-based liquid alkylation catalyst into a reactor where it contacts a continuous hydrocarbon phase containing effective amounts of olefinic and isoparaffinic starting materials sufficient for forming an alkylate product.

Once the alkylation reaction has gone to completion, the reaction mixture is sent to a separation vessel where the hydrocarbon phase, containing any unreacted material and the alkylate product, is separated from the catalyst. As previously mentioned, in conventional alkylation techniques, most of the separated catalyst is returned to the reaction zone without undergoing regeneration. Only a small portion of the total volume of separated catalyst is shunted away to the regeneration zone in a secondary path commonly referred to as a "slip stream".

Unlike conventional alkylation technology, the process of the present invention involves transferring the entire volume of separated catalyst into the regeneration zone for regeneration. The regenerated catalyst is subsequently returned to the reaction zone where it is redispersed into the hydrocarbon phase to perform further catalysis. Since the entire volume of catalyst is sent to the regeneration zone rather than directing a portion of the catalyst into a secondary "slip stream", the process of the present invention may be referred to as a "single path" alkylation.

As mentioned above, the hydrocarbon feedstock undergoing alkylation by the method of the present invention is provided to the reaction zone in a continuous hydrocarbon phase containing effective amounts of olefinic and isoparaffinic starting materials sufficient for forming an alkylate product. The olefin:isoparaffin ratio should range from about 1:1.5 to about 1:30, and preferably from about 1:5 to about 1:15. Higher isoparaffin-:olefin ratios may also be used, however limited availability of produced isoparaffin within the refinery coupled with the relatively high cost of recovering and recycling unconverted isoparaffin favor isoparaffin:olefin ratios within the ranges listed herein.

The olefin component should preferably contain 2 to 12 carbon atoms and the isoparaffin component should preferably contain 4 to 8 carbon atoms. Representative examples of suitable isoparaffins include isobutane, isopentane, 3-methylhexane, 2-methylhexane, 2,3-dimethylbutane and 2,4-dimethylhexane. Representative examples of suitable olefins include butene-2, isobutylene, butene-1, propylene, pentenes, ethylene, hexene, octene, and heptene, merely to name a few. The preferred olefins include the $C_4$ olefins, for example, butene-1, butene-2, isobutylene, or a mixture of one or more of these $C_4$ olefins, with butene-2 being the most preferred. Suitable feedstocks for the process of the present invention are described in U.S. Pat. No. 3,862,258 to Huang et al. at column 3, lines 44–56, the disclosure of which is incorporated by reference.

Unlike conventional alkylation technology wherein the hydrocarbon phase is typically dispersed into the acid phase, the process of the present invention involves dispersing an acid-based liquid alkylation catalyst into the reaction vessel for contact with a continuous hydrocarbon phase. Suitable liquid catalyst complexes include a Lewis acid together with at least one protic solvent having a pKa of less than about 16. Examples of such protic solvents include water, hydrogen sulfide, methanol, hexanoic acid, acetic acid, trifluoroacetic acid, phosphoric acid, pyrophosphoric acid, fluorophosphoric acid, ethanesulfonic acid, benzenesulfonic acid, sulfuric acid, sulfurous acid, hydrofluoric acid, hydrochloric acid, and hydrobromic acid. Two preferred catalysts for the present process include HF or $H_2SO_4$.

The density of the catalyst used in the present invention should exceed the density of the hydrocarbon effluent from the alkylation reaction zone to a degree sufficient for practical hydrocyclonic or gravitational separation of a less dense hydrocarbon layer from a more dense catalyst layer. Typical densities for the hydrocarbon phase range from about 0.6 g/cc to about 0.8 g/cc, and are usually below about 0.7 g/cc. Densities for the alkylation catalyst generally fall within the range of about 0.9 g/cc to about 2.0 g/cc.

Additionally, the liquid alkylation catalyst should exhibit no more than limited miscibility with the hydrocarbon products and reactants. Specifically the solubility of the liquid acid catalyst component in the hydrocarbon product and reactant phase should be less than about 3% by weight.

The amount of catalyst used in the present process can be varied over relatively wide limits. In general, the amount of catalyst as measured by the weight hourly space velocity of the olefin can range from about 0.01 to about 100. The amount of catalyst selected for a particular reaction will be determined by several variables including the reactants involved as well as the nature of the catalyst and the operating conditions used. Due to the unique single path continuous on-line regeneration of the entire volume of the separated catalyst, the total volume of catalyst required by the process of the present invention is drastically reduced. In particular, the total acid inventory in the reaction zone is 40 to 100 times less than in any existing alkylation technology. For example, in a unit producing approximately 5000 barrels per day of alkylate, the reactor vessel in a conventional alkylation technique typically contains between 5000 and 6000 gallons of catalyst as compared with 300 to 400 gallons of catalyst incorporated in the reactor vessel of the present invention.

Preferably, the process of the present invention should incorporate relative amounts of catalyst and hydrocarbon in a ratio ranging from about 0.01:1 to about 1:1, and more preferably in a ratio ranging from about 0.05:1 to about 0.5:1. In the most preferred embodiment of the present invention, the ratio of catalyst to hydrocarbon should range from about 0.1:1 to about 0.3:1.

Since the present process incorporates a liquid catalyst for catalyzing the alkylation reaction, the dispersion of catalyst into the continuous hydrocarbon phase is essentially a liquid-liquid dispersion wherein droplets of catalyst are delivered directly into contact with the hydrocarbon phase. Droplet size is an important process variable since it affects the extent of contact between the catalyst and the reaction mixture per unit time. Required residence time of the isoparaffin:olefin reactants is proportional to droplet size. As droplet size decreases, the power requirement to produce the droplets increases. Consequently, the incremental costs associated with reducing droplet size must be balanced against certain benefits, such as decreased catalyst inventory and reactor vessel volume.

In short, droplet size and contact times are important process variables which will depend to some degree upon the specific alkylation reaction being performed. These process conditions may, in turn, affect the characteristics of the resulting alkylate product and may be adjusted in accordance with parameters known to those skilled in the art. Preferably, the liquid catalyst incorporated in the method of the present invention is dispersed in droplets ranging from about 10 $\mu$m to about 5 mm, and more preferably from about 100 $\mu$m to about 700 $\mu$m. In the most preferred embodiment of the method of the present invention, the catalyst is dispersed in droplets ranging from about 200 $\mu$m to about 400 $\mu$m.

Additionally, the dispersion of the catalyst into the reaction zone should occur while maintaining the reactor vessel at a temperature ranging from about 0° F. to about 200° F., and more preferably from about 35° F. to about 130° F. Similarly, the pressure of the reactor vessel should be maintained at a level ranging from about 1 ATM to about 50 ATM, and more preferably from about 1 ATM to about 20 ATM. Most preferably, the reactor temperature should be maintained within a range from about 50° F. to about 110° F. and the reactor pressure should be maintained within a range from about 2 ATM to about 14 ATM. Suitable reactor vessels for performing the alkylation process of the present invention include back-mix reactors, plug flow reactors or the like.

In general, the particular operating conditions used in the process of the present invention will depend to some degree upon the specific alkylation reaction being performed. Process conditions such as temperature, pressure and space velocity as well as the molar ratio of the reactants will affect the characteristics of the resulting alkylate product and may be adjusted in accordance with parameters known to those skilled in the art.

Once the alkylation reaction has gone to completion, the reaction mixture is transferred to a suitable separation vessel where the hydrocarbon phase, containing the alkylate product and any unreacted reactants, is separated from the acid catalyst. Since the typical density for the hydrocarbon phase ranges from about 0.6 g/cc to about 0.8 g/cc and since densities for the alkylation catalyst generally fall within the ranges of about 0.9 g/cc to about 2.0 g/cc, the two phases are readily separable by conventional gravity settlers. Suitable gravitational separators include decanters. Hydrocyclones, which separate by density difference, are also suitable.

In a preferred embodiment of the method of the present invention, a hydrocyclonic separation technique is employed in order to promote the separation, thereby decreasing separation times. In particular, low pressure drop/low velocity hydrocyclones are induced by passing the reaction mixture through conical vessels located in the separation zone. Due to the configuration of the vessels, the flow velocity of the entering reaction mixture increases as the mixture progresses further into the vessels. The heavier substances, i.e. the acid phase, moves more rapidly to the outside of the vessel, thereby facilitating a decreased separation time. The use of hydrocyclonic separation has the advantage of very low acid inventory in the separation zone compared to conventional separation techniques. With hydrocyclones, the acid inventory in the separation zone may be as low as 50 gallons.

In accordance with the process of the present invention, the acid catalyst is removed from the separation vessel once adequate separation of the hydrocarbon phase and the catalyst has been completed. Unlike conventional alkylation technology which incorporates a secondary "slip stream" approach, the process of the present invention requires that the entire volume of separated catalyst be transported to the regeneration zone to undergo regeneration. This regeneration can be performed in accordance with any number of available techniques known to those skilled in the art. Once the regeneration has been completed the regenerated catalyst is returned to the reaction zone wherein it is redispersed into the hydrocarbon phase to perform further catalysis.

The following Example serves to further illustrate the present invention but is not meant in any way to limit or restrict the effective scope of invention.

EXAMPLE

In accordance with the present invention, an 18,000 BPD (barrels per day) single pass alkylation process is performed. A mixture of 65% weight HF and 35% weight additives (mainly sulfolane) is used as a catalyst. The catalyst to oil ratio is 0.083 volume per volume. Consequently, the HF to oil ratio is 0.05 volume per volume. The catalyst mixture, consisting of 190 gallons per minute of HF and 125 gallons per minute of additives, is dispersed into the hydrocarbon phase which consists of 3500 gallons per minute. The dispersion step should preferably be performed in a CSTR or plug flow reactor. The estimated reactor volume is approximately 6000 gallons, 300 gallons of which are HF. The resulting reaction mixture is sent to the separation area where the hydrocarbon phase is separated from the catalyst. Prior to separation, additional additives may be provided to the catalyst in order to generate an acid with an extremely low vapor pressure. Hydrocyclones are used to induce separation. Alternatively, hydrocyclones with low pressure drops of less than 50 psia and low liquid inlet velocities of less than 15 feet per second may also be employed. The entire volume of the recovered catalyst is sent to the regeneration area where the acid soluble oils are separated from the catalyst. The rate of regeneration for current technology is between 0.08 and 0.16 barrels of HF per barrel of alkylate. The rate of HF regeneration for the process of the present invention is about 0.36 barrels of HF per barrel of alkylate or 2 to 4 times higher than conventional techniques. The acid strength of the catalyst is adjusted to appropriate levels for the reaction zone and returned to the reactor accordingly.

While there have been described herein what are presently believed to be the preferred embodiments of the invention, those skilled in the art will realize that changes and modifications may be made thereto without departing from the spirit of the invention and it is intended to claim all such changes and modifications as fall within the true scope of the invention.

We claim:

1. A process for alkylating a hydrocarbon feedstock containing an olefin and an isoparaffin, said process comprising:

dispersing an acid-based liquid alkylation catalyst into a reaction zone containing a continuous hydrocarbon phase under conditions suitable for maintaining an alkylation reaction for contact with said continuous hydrocarbon phase containing an effective amount of an olefin and an isoparaffin sufficient for forming an alkylate product;

separating said continuous hydrocarbon phase from said catalyst upon formation of said alkylate product;

providing the entire volume of said separated catalyst to a regeneration zone; regenerating said separated catalyst in a continuous on-line regeneration in said regeneration zone to provide a regenerated catalyst; and returning said regenerated catalyst to said reaction zone.

2. A process according to claim 1, further comprising limiting the relative amounts of said catalyst and said hydrocarbon to a ratio from about 0.01:1 to 1:1.

3. A process according to claim 2, further comprising limiting said ratio from about 0.05:1 to about 0.5:1.

4. A process according to claim 3 further comprising limiting said ratio from about 0.1:1 to about 0.3:1.

5. A process according to claim 1, further comprising dispersing said catalyst in droplets ranging from about 10 $\mu$m to about 5 mm.

6. A process according to claim 5, further comprising limiting the size of said droplets from about 100 $\mu$m to about 700 $\mu$m.

7. A process according to claim 6, further comprising limiting the size of said droplets from about 200 $\mu$m to about 400 $\mu$m.

8. A process according to claim 1, further comprising limiting said isoparaffin to a carbon content ranging from 4 to 8 carbon atoms and limiting the olefin to a carbon content ranging from 2 to 12 carbon atoms.

9. A process according to claim 1, further comprising maintaining said reaction zone at a temperature ranging from about 0° F. to about 200° F.

10. A process according to claim 9, further comprising limiting said temperature to a range from about 35° F. to about 130° F.

11. A process according to claim 10, further comprising limiting said temperature to a range from about 50° F. to about 110° F.

12. A process according to claim 1, further comprising the maintaining said reaction zone at a pressure ranging from about 1 ATM to about 50 ATM.

13. A process according to claim 12, further comprising limiting said pressure to a range from about 1 ATM to about 20 ATM.

14. A process according to claim 13, further comprising limiting said pressure to a range from about 2 ATM to about 14 ATM.

15. A process according to claim 1, further comprising selecting said catalyst from the group consisting of HF and $H_2SO_4$.

16. A process according to claim 1, further comprising selecting said hydrocarbon feedstock such that said hydrocarbon phase contains said olefin and said isoparaffin in a ratio ranging from about 1:1.5 to about 1:30.

17. A process according to claim 16, further comprising selecting said hydrocarbon feedstock such that said hydrocarbon phase contains said olefin and said isoparaffin in a ratio ranging from about 1:5 to about 1:15.

18. A process according to claim 1, further comprising separating said hydrocarbon phase from said catalyst using hydrocyclonic separation.

* * * * *